United States Patent
Lu et al.

(10) Patent No.: US 7,244,751 B2
(45) Date of Patent: Jul. 17, 2007

(54) HISTONE DEACETYLASE INHIBITORS OF NOVEL BENZAMIDE DERIVATIVES WITH POTENT DIFFERENTIATION AND ANTI-PROLIFERATION ACTIVITY

(75) Inventors: Xian-Ping Lu, Guangdong (CN); Zhibin Li, Guangdong (CN); Aihua Xie, Guangdong (CN); Leming Shi, Guangdong (CN); Boyu Li, Guangdong (CN); Zhiqiang Ning, Guangdong (CN); Song Shan, Guangdong (CN); Tuo Deng, Guangdong (CN); Weiming Hu, Guangdong (CN)

(73) Assignee: Shenzhen Chipscreen Biosciences Ltd., Shenshen, Guangdong (CN)

( * ) Notice: Subject to any disclaimer, the term of this patent is extended or adjusted under 35 U.S.C. 154(b) by 504 days.

(21) Appl. No.: 10/770,035

(22) Filed: Feb. 2, 2004

(65) Prior Publication Data

US 2004/0224991 A1 Nov. 11, 2004

Related U.S. Application Data

(60) Provisional application No. 60/447,915, filed on Feb. 14, 2003.

(51) Int. Cl.
*A61K 31/44* (2006.01)
*A61K 31/16* (2006.01)
*C07C 233/00* (2006.01)
*C07D 211/70* (2006.01)

(52) U.S. Cl. ........................ 514/357; 514/613; 546/334; 564/155

(58) Field of Classification Search ................ 514/351, 514/357, 613; 546/334; 564/155
See application file for complete search history.

(56) References Cited

U.S. PATENT DOCUMENTS

2002/0103192 A1 8/2002 Curtin et al.
2002/0115716 A1 8/2002 Chaturvedi et al.

FOREIGN PATENT DOCUMENTS

EP 0847992 A1 6/1998

(Continued)

OTHER PUBLICATIONS

Ricky W. Johnstone, "Histone deacetylase inhibitors: novel drugs for the treatment of cancer," Nature Reviews Drug Discovery 2002, 1: 287-299.

(Continued)

*Primary Examiner*—Taylor Victor Oh
(74) *Attorney, Agent, or Firm*—Foley & Lardner LLP; Stephen E. Reiter

(57) ABSTRACT

The present invention is related to the preparation and pharmaceutical use of novel benzamide derivatives as defined in the specification of formula (I) as histone deacetylase inhibitors (HDACI), their preparations and the methods of using these compounds or their pharmaceutically acceptable salt in the treatment of cell proliferative diseases, e.g. cancer and psoriasis

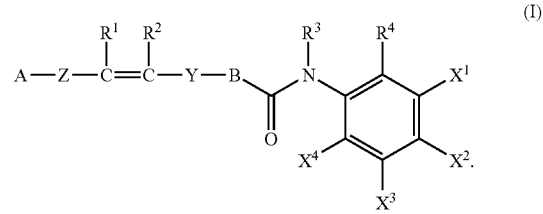

11 Claims, 1 Drawing Sheet

FOREIGN PATENT DOCUMENTS

| EP | 1170008 A1 | 1/2002 |
|---|---|---|
| WO | WO/0056153 A1 | 9/2000 |
| WO | WO/0118171 A2 | 3/2001 |
| WO | WO/0170675 A2 | 9/2001 |
| WO | WO/0226696 A1 | 4/2002 |

OTHER PUBLICATIONS

Paul A Marks, et al. "Histone deacetylase inhibitors as new cancer drugs," review Current Opinion in Oncology 2001, 13: 477-483.

Min-Hao Kuo, et al., "Roles of histone acetyltransferases and deacetylases in gene regulation," BioEssays 20: 615-626 (1998).

Korzus, E., et al., "Transcription Factor-Specific Requirements for Coactivators and Their Acetyltransferase Functions," www.sciencemag.org, SCIENCE, vol. 279, Jan. 30, 1998, 703-707.

Neil J. Mckenna, et al., "Combinatorial Control of Gene Expression by Nuclear Receptors and Coregulators," Cell, vol. 108, 465-474 (2000).

Michael J. Pazin, et al., "What's Up and Down with Histone Deacetylation and Transcription?" cell, vol. 89, May 2, 1997, 325-328.

Haihong Zhong, et al., Phosphoryltion of NF-kB p65 by PKA stimulates Transcriptional Acstivity by Promoting a Novel Bivalent Interaction with the Coactivator CBP/p300, Molecular Cell, vol. 1, Apr. 1998, 661-671.

J. S. Staffan, et al., Histone deacetylase inhibitors arrest polyglutamine-dependent neurodegeneration in Drosophia, Nature 2001, 413: 691-694.

Tony Kouzarides, "Histone acetylases and deacetylases in cell proliferation," Review, Current Opinion Genet. Development 1999, 9: 40-48.

Sandra Jacobson, et al., "Modifying chromatin and concepts of cancer," Current Opinion in Genetics & Development, 1999, 9: 175-184.

Richard J. Lin, et al., "Transcriptional regulation in acute promyelocytic leukemia," Oncogene, 2001, 20: 7204-7215.

W. Gu & Robert G. Roeder, "Activation of p53 Sequence-Specific DNA Binding by Acetylation of the p53 C-Terminal Domain," Cell, vol. 90, 595-606, Aug. 22, 1997.

Li-Jung Juan, et al., "Histone Deacetylases Specifically Down-regulate p53-dependent Gene Activation," The Journal of Biological Chemistry, vol. 275, No. 27, Jul. 7, 2000, pp. 20436-20443.

Abraham Nudelman, et al., Novel Mutual Prodrug of Retinoc and Butyric Acids with Enhanced Anticancer Activity. Journal of Mecial Chemistry, 2000, 43(15), 2962-2966.

Raymond P. Warrell, Jr., et al., "Therapeutic Targeting of Transcription in Acute Promyelocytic Leukemnia by Use of an Inhibitor of Histone Deacetylase," Journal of the National Cancer Institute, vol. 90, No. 21, Nov. 4, 1998, pp. 1621-1625.

Christopher J. Phiel, et al., "Histone Deacetylase is a Direct Target of Valproic Acid, a Potent Anticonvulsant, Mood Stabilizer, and Teratogen," The Journal of Biological Chemistry, vol. 276, No. 39, Sep. 28, 2001, pp. 36734-36741.

Akiko Saito, et al., "A synthetic inhibitor of histone deacetylase, MS-27-275, with marked in vivo antitumor activity against human tumors," Proc. Natl. Acad. Sci. USA, vol. 96, pp. 4592-4597, Apr. 1999.

E.B. Levit., "Clinical Trials in Leukemia focus on New Treatment Approaches," 2001 Release—Univ. of Maryland Medical News 2001, Maryland, http://www.umm.edu/news/releases/karp.html, A Phase I Study of an Oral Histone Deacetylase Inhibitor, MS-275, in Refactory Solid Tumors and Lymphomas. 2001, National Cancer Institute.

SEQUENCE LISTING

<160> NUMBER OF SEQ ID NOS: 3

<210> SEQ ID NO 1
<211> LENGTH: 68
<212> TYPE: DNA
<213> ORGANISM: human
<220> FEATURE:
<223> OTHER INFORMATION: GR

<400> SEQUENCE: 1
gatcttgtac aggatgttct ctagcgatgt acaggatgtt ctctagcgat gtacaggatg    60
ttctctag                                                             68

<210> SEQ ID NO 2
<211> LENGTH: 45
<212> TYPE: DNA
<213> ORGANISM: human
<220> FEATURE:
<223> OTHER INFORMATION: PPAR

<400> SEQUENCE: 2
cgcgttcctt tccgaacgtg acctttgtcc tggtcccctt ttgct                    45

<210> SEQ ID NO 3
<211> LENGTH: 26
<212> TYPE: DNA
<213> ORGANISM: human
<220> FEATURE:
<223> OTHER INFORMATION: ER

<400> SEQUENCE: 3
tcgagtcagg tcacagtgac ctgatc                                         26

HISTONE DEACETYLASE INHIBITORS OF NOVEL BENZAMIDE DERIVATIVES WITH POTENT DIFFERENTIATION AND ANTI-PROLIFERATION ACTIVITY

Priority is indicated herein from U.S. Provisional Application Ser. No. 60/447,915, filed Feb. 14, 2003.

FIELD OF THE INVENTION

The present invention relates to the preparation and use of novel benzamide derivatives as histone deacetylase inhibitors for treatments of differentiation- and/or proliferation-related disorders such as cancer and psoriasis.

BACKGROUND OF THE INVENTION

Aberrant expression of genes plays significant roles in the pathogenesis or pathological alterations in cancer, endocrine-related disorders, immune/inflammatory diseases, genetic diseases, and neurological diseases. The human genome is packaged into chromatin that consists of DNA, histones and non-histone proteins. Chromatin structure is an important factor in determining whether a particular gene is expressed or not. In general, condensed chromatin mediates transcriptional repression, whereas transcriptionally active genes are in areas of open chromatin. Nucleosomes form the basic repeating unit of chromatin, and consist of DNA wrapped around a histone octomer that is formed by four histone partners, namely an H3-H4 tetramer and two H2A-H2B dimmers. Histone H1 acts like a linker to stabilize the higher-order folding by electrostatic neutralization of the linker DNA segments through a positively charged carboxy-terminal domain. Therefore, the dynamic higher-order structure of nucleosomes defines distinct levels of chromatin organization and consequently, gene activation. Ricky W. Johnstone, "Histone deacetylase inhibitors: novel drugs for the treatment of cancer", *Nature Reviews Drug Discovery* 2002, 1: 287. The capacity of histone octomer to compact DNA is influenced by a number of post-translational modifications that occur on the N-terminal histone tails. One modification involves the reversible acetylation and deacetylation of the epsilon-amino group of lysine moieties found within the histone tails. The net level of acetylation of N-terminal histone tails is controlled by the activities of two families of enzymes, the histone acetyltransferases (HATs) and histone deacetylases (HDACs). In addition to HATs and HDACs, other factors also participate in determination of chromatin structure, including methyl-CpG-binding protein and adenosine triphosphate-depedent chromatin-remodeling complexes that can directly recruit HDACs, which leads to repression of gene activation (see review *Current Opinion in Oncology* 2001, 13:477-483).

The identification of coactivator complexes that possess intrinsic HAT activity strongly supports the connection between histone acetylation and transcriptional activation. Similarly, transcriptional repressor complexes have been shown to recruit HDACs to the promoter of target genes (*Bioassays* 1998, 20:615). Sequence-specific transcription factors, such as nuclear hormone receptor superfamily, cyclic adenosine 3', 5'-monophosphate-related enhancer binding protein (CREB), and signal transducer and activator of transcription-1 (STAT-1), interact with distinct coactivators and corepressors inside the complex of transcriptional machinery in a DNA-context and tissue-context selective fashion, resulting in selective regulation of gene expression networks. These regulatory networks govern homeostasis of our body's physiological functions and perturbation of those networks causes disorders and/or profoundly affects progression of diseases. Therefore, modulation of complex interactions of transcription machinery provides novel intervention strategies for the treatments of cancer, endocrine-related disorders, immune/inflammatory diseases, genetic diseases, and neurodegeneration (Korzus, E., et al., Transcription Factor-specific Requirements for Coactivator and Their Acetyltransferase Functions. *Science* 1998, 279: 703-707; McKenna, N. J. and B. W. O'Malley, Combinatorial Control of Gene Expression by Nuclear Receptors and Coregulators. *Cell* 2002, 108(4):465-474; Pazin, M. J. and J. T. Kadonaga, What's Up and Down with Histone Deacetylation and Transcription? *Cell* 1997, 89(3):325-328; Zhong, H., R. E. Voll, and S. Ghosh, Phosphorylation of NF-B p65 by PKA Stimulates Transcriptional Activity by Promoting a Novel Bivalent Interaction with the Coactivator CBP/p300. *Molecular Cell* 1998, 1(5):661-671; Steffan J S. et al., Histone deacetylase inhibitors arrest polyglutamine-dependent neurodegeneration in *Drosophila, Nature* 2001, 413: 691-694; HDAC inhibitor VX-563 from Vertex Pharmaceuticals proceeds for genetic disorders, 2002 EDGAR online News, US20020115716A1, WO0056153A1).

For instance, cell development and differentiation are governed by the hierarchical order of sequential gene activation, which is controlled at the level of chromatin structure. Genetic alterations or mutations that cause constitutive activation of oncoproteins such as RAS, or inactivation of tumor suppressors such as p53, affect a myriad of molecular programs, including transcription. In addition, genetic abnormalities that result in improper targeting of HATs and HDACs to certain loci, functional inactivation of HATs, overexpression of HDACs or epigenetic changes due to DNA hyper- and hypomethylation, can shift balance between cell development and differential programs that often lead to tumor onset and progression (see review *Current Opinion Genet. Development* 1999, 9: 40-48 and 175-184). Several human cancers have been associated with malfunctions in HAT and HDAC activity. One example is the translocation of chromosomes 15 and 17 seen in the majority of acute promyelocytic leukemia (APL) patients. In APL, chromosomal translocations produce fusion proteins that contain RARalpha, PML (promyelocytic leukaemia protein), and PLZF (promyelocytic zinc finger). These aberrant proteins bind to retinoic acid response elements, recruit HDACs with high affinity through enhanced binding for SMRT corepressor and are not responsive to retinoids, resulting in the constitutive repression of RAR-targeted genes (*Oncogene* 2001, 20:7204-7215). Retinoid acid receptor (RAR) is a ligand-activated transcriptional modulator that is important for myeloid differentiation. RAR heterodimerized with its partner RXR binds to retinoid acid response element, located in promoter region of target genes, and in the absence of retinoids, represses transcription by recruiting SIN3/HDAC through NCOR and SMRT corepressors. Addition of ligand releases the HDAC complexes from RAR/RXR, and allows subsequent binding of HATs, such as TIF2 and CBP, to activate transcription. Therefore, the coordinated activation and repression of genes that contain functional retinoid acid response elements is essential to myeloid cell differentiation. Furthermore, addition of HDAC inhibitors can restore sensitivity of APL cells to retinoid-induced myeloid cell differentiation, indicating that aberrant histone deacetylation is a key process in leukaemogenesis.

There are reports that histone deacetylases, when over-expressed, silence the expression of tumor suppressor genes that are natural brakes against tumor growth. For example, p53, a critical regulator of cell proliferation, transmits signals to genes that control the cell cycle and apoptosis when cells are under stress. The functions are principally controlled by the ability of p53 to bind to DNA with sequence-specificity and to activate transcription. Inactivation of this property of p53, mostly by mutations that occur in the central DNA-binding domain, often leads to malignancy. It has been demonstrated that CBP/p300 can up-regulate p53 through core histone acetylation and p53 acetylation. (W. Gu and R. G Roeder, Activation of p53 Sequence-Specific DNA Binding by Acetylation of the p53 C-Terminal Domain. *Cell* 1997, 90(4): 595-606.) Conversely, mammalian HDAC-1, HDAC-2, and HDAC-3 are shown to be capable of down-regulating p53 function by deacetylation of both core histone and p53 (Juan, L.-J., et al., Histone Deacetylases Specifically Down-regulate p53-dependent Gene Activation. *The Journal of Biological Chemistry* 2000, 275(27): 20436-20443).

These data show that inappropriate transcriptional repression mediated by HDACs is a common molecular mechanism that is used by oncoproteins, and alterations in chromatin structure can impinge on normal cellular differentiation, which leads to tumor formation and other hyperproliferative disorders. Therefore, the inhibition of HDAC activity seems to be a rational therapeutic pathway for cancers and other hyperproliferative diseases.

Several classes of HDAC inhibitors have been identified, including (1) short-chain fatty acids, e.g. butyrate and phenylbutyrate; (2) organic hydroxamic acids, e.g. suberoylanilide hydroxamic acid (SAHA) and trichostatin A (TSA); (3) cyclic tetrapeptides containing a 2-amino-8-oxo 9,10-expoxydecanoyl (AOE) moiety, e.g. trapoxin and HC-toxin; (4) cyclic peptides without the AOE moiety, e.g. apicidin and FK228; and (5) benzamides, e.g. MS-275 (EP0847992A1, US2002/0103192A1, WO02/26696A1, WO01/70675A2, WO01/18171A2).

Butyric acid acts as an inhibitor of cell proliferation and an inducer of cytodifferentiation due primarily to its activity of inhibiting histone deacetylase. (A. Nudelman and A. Rephaeli, Novel Mutual Prodrug of Retinoic and Butyric Acids with Enhanced Anticancer Activity. *J. Med. Chem.* 2000, 43(15): 2962-2966.) Phenylbutyrate has been used as a single agent in the treatment of β-thalassemia, toxoplasmosis, and malaria. It is also reported to be successful in treating refractory APL in combination with RA (retinoid acid). (R. P. Warrell. et al., Therapeutic targeting of transcription in acute promyelocytic leukemia by use of an inhibitor of histone deacetylase. *J. Natl. Cancer Inst.* 1998, 90(21): 1621-1625.) Another fatty acid, valproic acid, which is a potent anticonvulsant, mood stabilizer and teratogen, is also a direct inhibitor of histone deacetylase. (C. J. Phiel et al., Histone Deacetylase Is a Direct Target of Valproic Acid, a Potent Anticonvulsant, Mood Stabilizer, and Teratogen. *The Journal of Biological Chemistry* 2001, 276(39): 36734-36741; EP1170008A1).

A set of benzamides was discovered to have HDAC inhibitory activity in the low micromolar range. A lead compound, MS-275, from this set of benzamides is being tested by Mitsui Chemicals, Inc. and it is the first HDAC inhibitor to demonstrate oral anticancer activity in animal models with no severe side effects. (A. Saito et al., A synthetic inhibitor of histone deacetylase, MS-27-275, with marked in vivo antitumor activity against human tumors. *Proceedings of the National Academy of Sciences of the United States of America* 1999, 96(8): 4592-4597; EP 0847992 A1). MS-275 is currently under clinical trials in the University of Maryland Greenebaum Cancer Center for leukemia patients and by the U.S. National Cancer Institute for advanced solid tumors. (E. B. Levit, Clinical Trials in Leukemia focus on New Treatment Approaches. 2001 Release—University of Maryland Medical News 2001 Maryland http://www.umm.edu/news/releases/karp.html, A Phase I Study of an Oral Histone Deacetylase Inhibitor, MS-275, in Refractory Solid Tumors and Lymphomas. 2001, National Cancer Institute). However, there is still a need to discover new compounds with improved profiles, such as stronger HDAC inhibitory activity.

SUMMARY OF THE INVENTION

The current invention provides compounds that exhibit differentiation-inducing and proliferation-inhibiting effects and are useful as therapeutic treatment or improving agents for disorders related to differentiation and/or proliferation, such as cancer and psoriasis. In particular, they are highly effective against hematological malignancy and solid carcinoma.

DETAILED DESCRIPTION OF THE INVENTION

Figure 1:
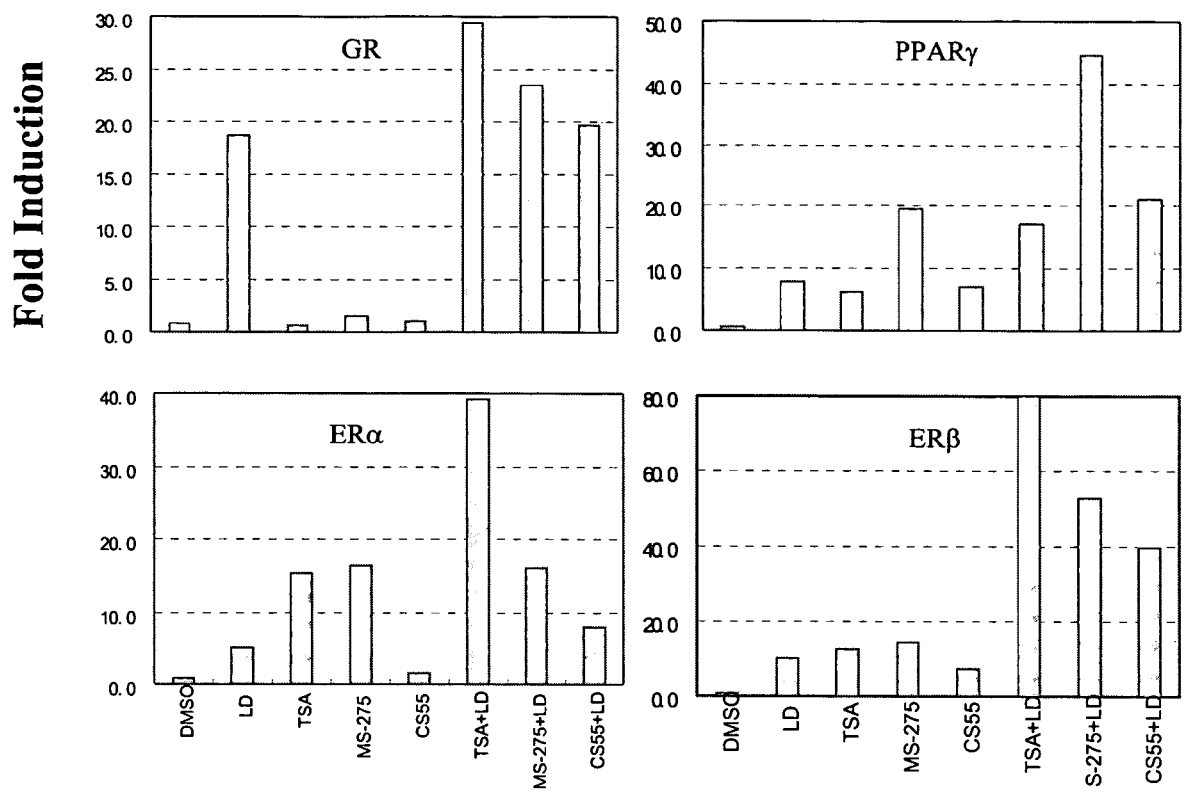
FIG. 1 graphically demonstrates the transcriptional activation of various nuclear hormone receptors by example HDAC inhibitors, i.e., Trichostatin A, MS-275 as well as an example compound of the present invention.

Various publications are cited throughout the present application. The contents of these publications and contents of documents cited in these publications are herein incorporated herein by reference.

The present invention provides compounds represented by formula (I), or its stereoisomer, enantiomer, diastereomer, hydrate, or pharmaceutically acceptable salts thereof:

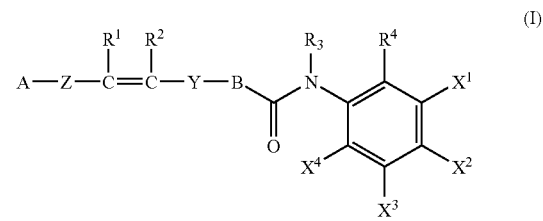

wherein A is a phenyl or heterocyclic group, optionally substituted with 1 to 4 substituents selected from the group consisting of a halogen atom, a hydroxyl group, an amino group, a nitro group, a cyano group, an alkyl group having 1 to 4 carbons, an alkoxy group having 1 to 4 carbons, an aminoalkyl group having 1 to 4 carbons, an alkylamino group having 1 to 4 carbons, an acyl group having 2 to 4 carbons, an acylamino group having 2 to 4 carbons, an alkythio group having 1 to 4 carbons, a perfluoroalkyl group having 1 to 4 carbons, a perfluoroalkyloxy group having 1 to 4 carbons, a carboxyl group, an alkoxycarbonyl group having 1 to 4 carbons, a phenyl group and a heterocyclic group;

B is a phenyl or heterocyclic group, optionally substituted with 1 to 3 substituents selected from the group consisting of a halogen atom, a hydroxyl group, an amino group, a nitro group, a cyano group, an alkyl group having 1 to 4 carbons, an alkoxy group having 1 to 4 carbons, an aminoalkyl group having 1 to 4 carbons, an alkylamino group having 1 to 4 carbons, an acyl group having 2 to 4 carbons, an acylamino group having 2 to 4 carbons, an alkythio group having 1 to 4 carbons, a perfluoroalkyl group having 1 to 4 carbons, a perfluoroalkyloxy group having 1 to 4 carbons, a carboxyl group, an alkoxycarbonyl group having 1 to 4 carbons, a phenyl group and a heterocyclic group;

Z is a bond, an optionally substituted alkylene having 1 to 4 carbons or a moiety having —O—, —S—, —NH—, —CO—, —CS—, —SO— or —$SO_2$— which is linear, cyclic or their combination;

Y is a moiety having —CO—, —CS—, —SO— or —$SO_2$— which is linear, cyclic or their combination; and in which the distances between the centroid of ring B (W1), the centroid of ring A (W2) and an oxygen or sulfur atom as a hydrogen bond acceptor in the moiety Y (W3) can, for example, be as follows: W1-W2=6.0 to 12.0 Å, W1-W3=3.0 to 6.0 Å, and W2-W3=4.0 to 8.0 Å; preferably W1-W2=8.0 to 10.0 Å, W1-W3=3.0 to 5.0 Å, W2-W3=5.0 to 8.0 Å (compounds of the invention described herein, however, are not necessarily limited to these dimensions);

$R^1$ and $R^2$ are independently a hydrogen or an optionally substituted alkyl having 1 to 4 carbons; or $R^1$ and $R^2$ may form a bond;

$R^3$ is a hydrogen or an optionally substituted alkyl having 1 to 4 carbons; $R^4$ is a hydrogen atom, halogen atom, a hydroxyl group, an amino group, a nitro group, a cyano group, an alkyl group having 1 to 4 carbons, an alkoxy group having 1 to 4 carbons, an aminoalkyl group having 1 to 4 carbons, an alkylamino group having 1 to 4 carbons, an acyl group having 1 to 4 carbons, an acylamino group having 1 to 4 carbons, an alkylthio group having 1 to 4 carbons, a perfluoroalkyl group having 1 to 4 carbons, a perfluoroalkyloxy group having 1 to 4 carbons, a carboxyl group or an alkoxycarbonyl group having 1 to 4 carbons.

One of $X^1$, $X^2$, $X^3$, or $X^4$ is a halogen atom, a hydroxyl group, an amino group, a nitro group, a cyano group, an alkyl group having 1 to 4 carbons, an alkoxy group having 1 to 4 carbons, an aminoalkyl group having 1 to 4 carbons, an alkylamino group having 1 to 4 carbons, an acyl group having 1 to 4 carbons, an acylamino group having 1 to 4 carbons, an alkylthio group having 1 to 4 carbons, a perfluoroalkyl group having 1 to 4 carbons, a perfluoroalkyloxy group having 1 to 4 carbons, a carboxyl group or an alkoxycarbonyl group having 1 to 4 carbons, while the others of $X^1$, $X^2$, $X^3$, or $X^4$ independently are a hydrogen atom, a halogen atom, a hydroxyl group, an amino group, a nitro group, a cyano group, an alkyl group having 1 to 4 carbons, an alkoxy group having 1 to 4 carbons, an aminoalkyl group having 1 to 4 carbons, an alkylamino group having 1 to 4 carbons, an acyl group having 1 to 4 carbons, an acylamino group having 1 to 4 carbons, an alkylthio group having 1 to 4 carbons, a perfluoroalkyl group having 1 to 4 carbons, a perfluoroalkyloxy group having 1 to 4 carbons, a carboxyl group or an alkoxycarbonyl group having 1 to 4 carbons.

In the above structural formula (I) and throughout the present specification, the following terms have the indicated meaning:

The term "heterocyclyl" as used herein means a monovalent saturated or unsaturated group being monocyclic and containing one or more heteroatoms, such as pyrrolidine, pyrroline, pyrazoline, imidazolidine, imidazoline, piperidine, morpholine and the like.

The term "halogen" as used herein means fluorine, chlorine, bromine or iodine.

The term "alkyl having 1 to 4 carbons" as used herein includes methyl, ethyl, n-propyl, iso-propyl, butyl, iso-butyl, sec-butyl and tert-butyl.

The term "alkoxy having 1 to 4 carbons" as used herein includes methoxy, ethoxy, n-propoxy, isopropoxy, n-butoxy, isobutoxy and the like.

The term "aminoalkyl having 1 to 4 carbons" as used herein includes aminomethyl, 1-aminopropyl, 2-aminopropyl and the like.

The term "alkylamino having 1 to 4 carbons" as used herein includes N-methylamino, N-ethylamino, N-isopropylamino and the like.

The term "acyl having 2 to 4 carbons" as used herein includes acetyl, propionyl, butyryl, isobutyryl and the like.

The term "acylamino having 2 to 4 carbons" as used herein includes acetylamino, propionylamino, butyrylamino, isobutyrylamino and the like.

The term "alkylthio having 2 to 4 carbons" as used herein includes methylthio, ethylthio, propylthio and the like.

The term "perfluoroalkyl having 2 to 4 carbons" as used herein includes trifluoromethyl, pentafluoroethyl and the like.

The term "perfluoroalkyloxy having 2 to 4 carbons" as used herein includes trifluoromethoxy, pentafluoroethoxy and the like.

The term "alkylene having 1 to 4 carbons" as used herein includes methylene, ethylene and the like.

The term "ring centroid" used in definition of the spatial configuration may be defined as an average of X, Y and Z axes of the ring-forming atoms.

The compounds of this invention are prepared as described below:

(a) A compound represented by formula (II) is condensed with a compound represented by formula (III) to give a compound represented by formula (IV):

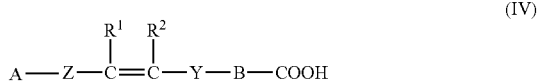

wherein A, Z, Y, B, $R^1$ and $R^2$ are as defined above; $R^5$ is a moiety having —C(=Q)OH (Q is an oxygen or sulfur atom) or a moiety having —$NH_2$; $R^6$ is a moiety having —$NH_2$ when $R^5$ is a moiety having —C(=Q)OH (Q is an oxygen or sulfur atom) and a moiety having —C(=Q)OH (Q is an oxygen or sulfur atom) when $R^5$ is a moiety having —$NH_2$.

(b) A compound represented by formula (IV) is condensed with a compound represented by formula (V) to give the compound of this invention.

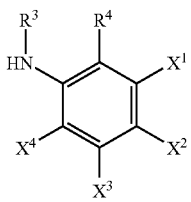

(V)

wherein $R^3$, $R^4$, $X^1$, $X^2$, $X^3$, and $X^4$ are as defined above.

The above condensation reactions (a) and (b) are conducted using a peptide condensing agent such as dicyclohexylcarbodiimide, N,N'-carbonyldiimidazole, diphenyl phosphoric azide, diethylphosphorylcyanide, etc.

The reaction may be conducted at 0 to 80° C. for 4 to 72 hours. Solvents which may be used are normal solvents such as benzene, toluene, tetrahydrofuran, dioxane, dichloromethane, chloroform, N,N-dimethylformamide, etc. If necessary, a base such as sodium hydroxide, triethylamine and pyridine or an acid such as hydrochloric acid, acetic acid and trifluoroacetic acid may be added to the reaction system.

The compound of this invention and the intermediate represented by formula (I) may be purified or isolated by the conventional separation method such as extraction, recrystallization, column chromatography and the like.

The novel compounds of this invention have differentiation-inducing effects and thus are useful as therapeutic treatment or improving agents related to differentiation and/or proliferation-related disorders such as cancer and psoriasis. In particular, they are highly effective as carcinostatic agents to hematological malignancy and solid carcinoma.

The active ingredient of this invention useful as a drug may be used in the form of a general pharmaceutical composition. The pharmaceutical composition may be in the forms normally employed, such as tablets, capsules, powders, syrups, solutions, suspensions, aerosols, and the like, may contain flavourants, sweeteners, etc. in suitable solids or liquid carriers or diluents, or in suitable sterile media to form injectable solutions or suspensions. Such composition typically contains from 1 to 70%, preferably 5 to 50% by weight of active compound, the remainder of the composition being pharmaceutically acceptable carriers, diluents or solvents or salt solutions.

The compounds of this invention are clinically administered to mammals, including man and animals, via oral, nasal, transdermal, pulmonary, or parenteral routes. Administration by the oral route is preferred, being more convenient and avoiding the possible pain and irritation of injection. By either route, the dosage is in the range of about 0.0001 to about 200 mg/kg body weight per day administered singly or as a divided dose. However, the optimal dosage for the individual subject being treated will be determined by the person responsible for treatment, generally smaller doses being administered initially and thereafter increments made to determine the most suitable dosage.

The following examples are given as specific illustrations of the invention. It should be understood, however, that the invention is not limited to the specific details set forth in the examples. All parts and percentages in the examples, as well as in the remainder of the specification, are by weight unless otherwise specified.

Further, any range of numbers recited in the specification or paragraphs hereinafter describing or claiming various aspects of the invention, such as that representing a particular set of properties, units of measure, conditions, physical states or percentages, is intended to literally incorporate expressly herein by reference or otherwise, any number falling within such range, including any subset of numbers or ranges subsumed within any range so recited. The term "about" when used as a modifier for, or in conjunction with, a variable, is intended to convey that the numbers and ranges disclosed herein are flexible and that practice of the present invention by those skilled in the art using temperatures, concentrations, amounts, contents, carbon numbers, and properties that are outside of the range or different from a single value, will achieve the desired result.

EXAMPLE 1

Preparation of 4-[N-(Pyridin-3-ylacryloyl)aminomethyl]benzoic acid

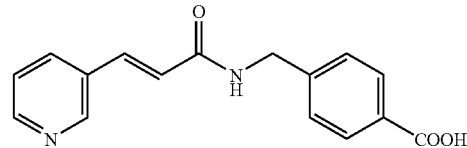

To a suspension of 0.33 g (2.01 mmol) of N,N'-carbonyldiimidazole in tetrahydrofunan (10 ml) is added drop-wise a solution of 0.30 g (2.01 mmol) of 3-pyridineacrylic acid at 0° C. Then, the mixture is stirred at room temperature for 3 hours and added drop-wise to a separately prepared 2.0 ml (2.00 mmol) of 1N aqueous sodium hydroxide solution including 0.30 g (2.00 mmol) of 4-aminomethylbenzoic acid, followed by stirring at room temperature for 8 hours. The reaction mixture is evaporated under vacuum. To the residue is added a saturated solution of sodium chloride (2 ml), then the mixture is neutralized with concentrated hydrochloric acid to pH 5. The deposited white solid is collected by filtration, washed with ice-water, and then dried to give the title compound (0.46 g, 82%). HRMS calcd for $C_{16}H_{14}N_2O_3$: 282.2988. Found: 282.2990. MA calcd for: $C_{16}H_{14}N_2O_3$: C, 68.07%; H, 5.00%; N, 9.92%. Found: C, 68.21%; H, 5.03%; N, 9.90%.

EXAMPLE 2

Preparation of N-(2-amino-4-fluorophenyl)-4-[N-(Pyridn-3-ylacryloyl)aminomethyl]benzamide

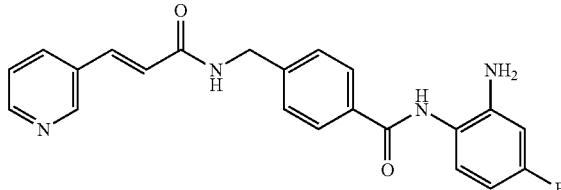

To a suspension of 0.29 g (1.78 mmol) of N,N'-carbonyldiimidazole in tetrahydrofunan (15 ml) is added 0.50 g (1.78 mmol) of 4-[N-(Pyridn-3-ylacryloyl)aminomethyl]benzoic acid), followed by stirring at 45° C. for 1 hour. After cooling, the reaction mixture is added to a separately prepared tetrahydrofuran (10 ml) solution including 0.28 g (2.22 mmol) of 4-fluoro-1,2-phenylenediamine and 0.20 g (1.78 mmol) of trifluoroacetic acid at room temperature. After reaction at room temperature for 24 hours, the deposited white solid is collected by filtration, washed with tetrahydrofuran, and then dried to give the title compound (0.40 g, 57%). $^1$H NMR (300 MHz, DMSO-d$_6$): δppm: 4.49 (2H, d), 4.84 (2H, br.s), 6.60 (1H, t), 6.80 (2H, m),696 (1H, t), 7.18 (1H, d), 7.42 (2H, d), 7.52 (1H, d), 7.95 (2H, d), 8.02 (1H, d), 8.56 (1H, d), 8.72 (1H, br. t), 8.78 (1H, s), 9.60 (1H, br.s). IR (KBr) cm$^1$: 3310, 1655, 1631, 1524, 1305, 750. HRMS calcd for $C_{22}H_{19}N_4O_2F$: 390.4170. Found: 390.4172. MA calcd for $C_{22}H_{19}N_4O_2F$: C, 67.68%; H, 4.40%; N, 14.35%. Found: C, 67.52%; H, 4.38%; N, 14.42%.

EXAMPLE 3

Preparation of 4-[N-cinnamoylaminomethyl]benzoic acid

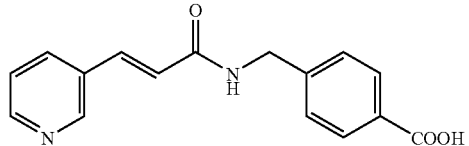

To a suspension of 0.33 g (2.01 mmol) of N,N'-carbonyldiimidazole in tetrahydrofuran (10 ml) is added drop-wise a solution of 0.30 g (2.01 mmol) of cinnamic acid at 0° C. Then, the mixture is stirred at room temperature for 3 hours and added drop-wise to a separately prepared 2.0 ml (2.00 mmol) of 1N aqueous sodium hydroxide solution including 0.30 g (2.00 mmol) of 4-aminomethylbenzoic acid, followed by stirring at room temperature for 8 hours. The reaction mixture is evaporated under vacuum. To the residue is added a saturated solution of sodium chloride (2 ml), then the mixture is neutralized with concentrated hydrochloric acid to pH 7. The deposited white solid is collected by filtration, washed with ice-water, and then dried to give the title compound (0.51 g, 91%). HRMS calcd for $C_{17}H_{15}NO_3$: 281.3242. Found: 281.3240. MA calcd for $C_{17}H_{15}NO_3$: C, 72.58%; H, 5.38%; N, 4.98. Found: C, 72.42%; H, 5.37%; N, 4.98%.

EXAMPLE 4

Preparation of N-(2-amino-4-fluorophenyl)-4-[N-cinnamoylaminomethyl]benzamide

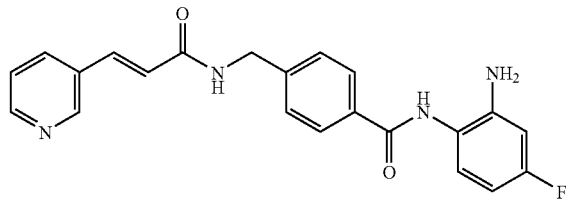

To a suspension of 0.29 g (1.78 mmol) of N,N'-carbonyldiimidazole in tetrahydrofuran (15 ml) is added 0.50 g (1.78 mmol) of 4-[N-cinnamoylaminomethyl]benzoic acid, followed by stirring at 45° C. for 1 hour. After cooling, the reaction mixture is added to a separately prepared tetrahydrofuran (10 ml) solution including 0.28 g (2.22 mmol) of 4-fluoro-1,2-phenylenediamine and 0.20 g (1.78 mmol) of trifluoroacetic acid at room temperature. After reaction at room temperature for 16 hours, the deposited white solid is collected by filtration, washed with tetrahydrofuran, and then dried to give the title compound (0.45 g, 64%). $^1$H NMR (300 MHz, DMSO-d$_6$): δppm: 4.42 (2H, d), 4.92 (2H, br.s), 6.62 (1H, t), 6.78 (2H, m), 7.01 (1H, t), 7.32 (5H, m), 7.54 (5H, m), 8.76 (1H, br.t), 9.58 (1H, br.s). IR (KBr) cm$^{-1}$: 3306, 1618, 1517, 1308, 745. HRMS calcd for $C_{23}H_{20}N_3O_2F$: 389.4292. Found: 389.4294. MA calcd for $C_{23}H_{20}N_3O_2F$: C, 70.94%; H, 5.18%; N, 10.79%. Found: C, 70.72%; H, 5.18%; N, 10.88%.

EXAMPLE 5

In vitro inhibition of HDAC enzymatic activity by N-(2-amino-4-fluorophenyl)-4-[N-(Pyridin-3-ylacryloyl)aminomethyl]benzamide (Compound CS02100055), N-(2-aminophenyl)-4-[N-(4-fluorophenyl)aminomethyl]benzamide (compound CS02100019), and N-(2-aminophenyl)-4-[N-(pyridin-3-ylmethoxycarbonyl) aminomethyl]benzamide (MS-275, EP0847992).

The inhibitory effects of MS-275 and compounds CS02100055 and CS02100019 on HDAC were tested by a HDAC calorimetric activity assay kit (BIOMOL Research Laboratories, PA, USA) according to the instructions from the manufacturer. Briefly, the tested compounds at different concentrations were added to 96-well plates, then mixed with extract from HeLa cells containing HDAC activity provided by the manufacturer. HDAC reactions were initiated by adding substrate. 10 minutes later, the reactions were stopped by addition of Color De Lys Developer. Microplates were read in a plate reader at 405 nm. Inhibition of HDAC activity was calculated following the instructions. The testing results are listed in Table 1.

TABLE 1

In vitro Inhibition of HDAC Activity by MS275, CS02100055 and CS02100019

| Compound | % of inhibition of HDAC activity concentrations | | | | $IC_{50}$ (μM) |
|---|---|---|---|---|---|
| | 1 μM | 5 μM | 10 μM | 50 μM | |
| MS-275 | 14.7 | 19.1 | 64.1 | 82.3 | 8.4 |
| CS02100055 | 17.5 | 37.3 | 62.1 | 78.4 | 7.2 |
| CS02100019 | 11.3 | 24.9 | 28.4 | 29.8 | >50.0 |

EXAMPLE 6

The growth inhibitory effect of N-(2-amino-4-fluorophenyl)-4-[N-(Pyridin-3-ylacryloyl)aminomethyl]benzamide (Compound CS02100055), N-(2-aminophenyl)-4-[N-(4-fluorophenyl)aminomethyl]benzamide (Compound CS02100019), and N-(2-aminophenyl)-4-[N-(pyridin-3-ylmethoxycarbonyl) aminomethyl]benzamide (MS-275, EP0847992), on various tumor cell lines in vitro.

Growth inhibition tests were carried out by MTS method. Approximately 72 hours before the viability assay, cells were seeded into 96-well plates at 5-10×10$^3$ cells/well (according to the growth rate of individual cell lines used). 24 hours later, the tested compounds at different concentrations were added, and the cells were cultured for 48 hours, then added 20 μl/well of CellTiter 96 AQueous One Solution Reagent containing tetrazolium compound (Promega) into each well. MTS was subsequently added to the culture medium. After incubation of the plates for 2 hours at about 37° C., the absorbance at 490 nm was recorded by a 96-well plate reader. Cell viability was calculated by $A_{treatment}/A_{control} \times 100\%$ (A represents the absorbance recorded at 490 nm). The concentration that inhibited cell growth by 50% over the control was determined as $GI_{50}$. All of the compounds were dissolved in DMSO and were added to the culture at a 1:1000 dilution to give a final DMSO concentration of $\leq 0.1\%$. All samples were assayed in duplicate, and each experiment was repeated at least three times. The testing results are summarized in Table 2.

reagent according to the manufacturers instructions (Roche). Cells were allowed to express protein for 24 hours followed by addition of individual compounds or the vehicle (DMSO). 24 hours later cells were harvested, and the luciferase assays were performed using the luciferase assay kit according to the manufacturer's instructions (Promega). To normalize the data from the luciferase assays, β-galactosidase activity from transfected cells was measured using a kit (Promega) as instructed by the manufacturer. Response elements for individual unclear receptors were as following:

TABLE 2

Growth Inhibition of Tumor Cell lines by MS-275, CS2100055 and CS02100019

| | $GI_{50}$ (μM) against Various Tumor Cell Lines* | | | | | | | | |
|---|---|---|---|---|---|---|---|---|---|
| Compound | U2OS | HeLa | DU-145 | SMMC-721 | HepG2 | 293 | MCF-7 | 231 | H292 |
| MS-275 | 1.0 | 25 | 13 | 20 | 3.2 | 16 | 6.3 | 5.0 | 16 |
| CS02100055 | 2.0 | 40 | 25 | 16 | 4.0 | 50 | 5.0 | 7.9 | 50 |
| CS02100019 | 2.5 | 50 | 50 | 50 | 3.2 | 25 | 5.0 | 7.9 | 50 |

| | $GI_{50}$ (μM) against Various Tumor Cell Lines* | | | | | | | | |
|---|---|---|---|---|---|---|---|---|---|
| Compound | LNCaP | SK-N-SH | PANC-1 | SK-OV-3 | SGC-7901 | Raji | HL-60 | 28SC | Jurkat |
| MS-275 | 2.5 | 50 | 5.0 | 50 | 50 | 6.3 | 0.32 | 4.0 | 1.6 |
| CS02100055 | 4.0 | 50 | 6.3 | 50 | 50 | 4.0 | 0.4 | 5.8 | 1.5 |
| CS02100019 | 10 | 50 | 5.0 | 50 | 50 | 2.0 | 0.5 | 2.0 | 1.0 |

*Origin of the cell lines:
U2OS, human osteocarcinoma
HeLa, human cervical carcinoma
DU-145, human prostate cancer
SGC-7901, human gastric adenocarcinoma
SMMC-7721, human hepatoma
HepG2, human hepatoblastoma
293, human embryonic kidney
MCF-7, human breast adenocarcinoma
MDA-MB-231, human breast adenocarcinoma
H292, human lung cancer
LNCaP, human prostate cancer
SK-N-SH, human neuroblastoma
PANC-1, human pancreatic ductal carcinoma
SK-OV-3, human ovary adenocarcinoma
28SC, human macrophage
Raji, human Burkitts Lymphoma
HL-60, human myloid leukemia
Jurkat, human T cell leukemia

EXAMPLE 7

Transcription activation of nuclear hormone receptors by N-(2-amino-4-fluorophenyl)-4-[N-(Pyridin-3-ylacryloyl) aminomethyl]benzamide (Compound CS02100055), N-(2-aminophenyl)-4-[N-(pyridin-3-ylmethoxycarbonyl) aminomethyl]benzamide (MS-275, EP0847992) and Trichostatin A (TSA).

Transcription activation of several nuclear hormone receptors by tested compounds, as indicated in FIG. 1, was carried out by reporter assay experiments. Briefly, U2OS cells were seeded in 96-well plates the day before transfection to give a confluency of 50-80%. Cells were transfected with one of the expression plasmids containing cDNAs coding either glucocorticoid receptor (GR), peroxisome proliferator activated receptor γ (PPARγ, estrogen receptor α (ERα), or estrogen receptor β (ER β), in combination with retinoid X receptor α (RXR α), and their corresponding luciferase reporter plasmids using FuGene6 transfection GR (5'-GATCTTGTACAGGATGTTCTCTAGCGATGTACAGGATGTTCTCTAGCGATG TACAGGATGTTCTCTAG-3') (SEQ ID NO. 1), PPAR (5'-CGCGTTCCTTTCCGAACGTGACCTTTGTCCTGGTCCCCTTTTGCT-3') (SEQ ID NO. 2), and ER (5'-TCGAGTCAGGTCACAGTGACCTGATC-3') (SEQ ID NO. 3). The testing results are summarized in FIG. 1. FIG. 1 shows transcription activation of nuclear hormone receptors by different HDAC inhibitors Trichostatin A, MS-275 and CS2100055. Experiments were carried out as described above. LD stands for corresponding Ligands for each receptor, and CS55 for CS2100055 in each panel of the FIGURE. Concentrations of tested compounds in all experiments were TSA 0.2 μM, MS-275 1 μM, and CS55 1 μM. Dexamethasone (0.1 μM), Rosiglitazone (10 μM), and E2 (0.01 μM) were used as ligands for GR, PPARγ, and ER, respectively. Three independent experiments were performed and the results from a representative experiment were shown in FIG. 1.

What is claimed is:

1. A compound of formula I:

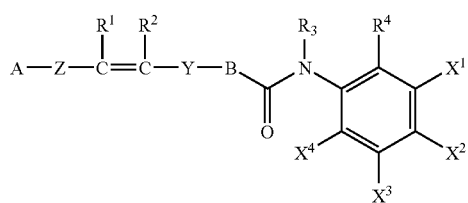

(I)

or its stereoisomer, enantiomer, diastereomer, or a pharmaceutically acceptable salt; wherein A is a phenyl or pyridyl, optionally substituted with 1 to 4 substituents selected from the group consisting of a halogen atom, an alkyl group having 1 to 4 carbons, and a perfluoralkyl group having 1 to 4 carbons;

B is-phenyl;

Z is a bond;

Y is a moiety having —CO— which is linear and in which the distances between the centroid of ring B (W1), the centroid of ring A (W2) and an oxygen atom as a hydrogen bond acceptor in the moiety Y (W3) are: W1-W2=about 6.0 to about 12.0 Å, W1-W3=about 3.0 to about 6.0 Å, and W2-W3=about 4.0 to about 8.0 Å, respectively;

$R^1$ and $R^2$ are independently hydrogen or an alkyl having 1 to 4 carbons;

$R^3$ is hydrogen;

$R^4$ is an amino group; and

One of $X^1$, $X^2$, $X^3$, or $X^4$ is halogen or an alkyl group having 1 to 4 carbons while the others of $X^1$, $X^2$, $X^3$, or $X^4$ independently are hydrogen.

2. A process for the preparation of a compound according to claim 1 or its stereoisomer, enantiomer, diastereomer, or pharmaceutically acceptable salt thereof comprising the steps of:

(a) condensing a compound represented by formula (II) with a compound represented by formula (III) to yield a compound represented by formula (IV):

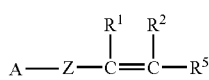

(II)

(III)

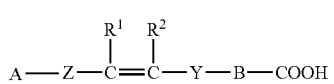

(IV)

$R^5$ is a moiety having —C(=Q)OH wherein Q is an oxygen; $R^6$ is a moiety having —NH$_2$; and (b) condensing the compound represented by formula (IV) with a compound represented by formula (V) to give the compound of formula (I);

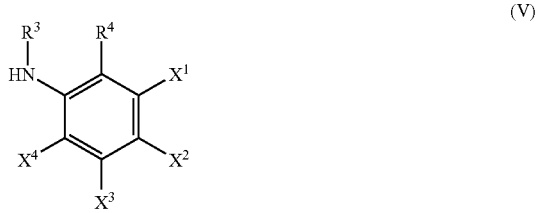
(V)

wherein one of $X^1$, $X^2$, $X^3$, or $X^4$ is a halogen atom or an alkyl group having 1 to 4 carbons and the other of $X^1$, $X^2$, $X^3$, or $X^4$ independently are hydrogen;
$R^3$ is hydrogen; and
$R^4$ is an amino group.

3. The process according to claim 2, wherein the condensation reactions of steps (a) and (b) are carried out using a peptide condensing agent.

4. The process according to claim 3, wherein said peptide condensing agent is dicyclohexylcarbodiimide, N,N'-carbonyldiimidazole, diphenyl phosphoric azide, or diethylphosphorylcyanide.

5. The process of claim 2, wherein said condensation reactions of steps (a) and (b) are conducted at a temperature from about 0° C. to about 80° C.

6. A pharmaceutical composition comprising an effective amount of a compound according to claim 1 and at least one pharmaceutically acceptable excipient, carrier or diluent.

7. A dosage form unit of the pharmaceutical composition of claim 6 comprising an amount within the range of about 0.0001 to about 200 mg of said compound.

8. A pharmaceutical composition according to claim 6 for administration by the oral, nasal, transdermal, pulmonary, or parenteral route.

9. A pharmaceutical composition for activating nuclear receptors comprising an effective amount of a compound according to claim 1 and at least one a pharmaceutically acceptable excipient, carrier or diluent.

10. A dosage form unit of the pharmaceutical composition of claim 9 comprising an amount within the range of about 0.0001 to about 200 mg of the compound.

11. A pharmaceutical composition according to claim 9 for administration by the oral, nasal, transdermal, pulmonary, or parenteral route.

* * * * *

UNITED STATES PATENT AND TRADEMARK OFFICE
CERTIFICATE OF CORRECTION

PATENT NO. : 7,244,751 B2 Page 1 of 1
APPLICATION NO. : 10/770035
DATED : July 17, 2007
INVENTOR(S) : Xian-Ping Lu et al.

It is certified that error appears in the above-identified patent and that said Letters Patent is hereby corrected as shown below:

IN THE SPECIFICATION:

Column 9, lines 20-28, " 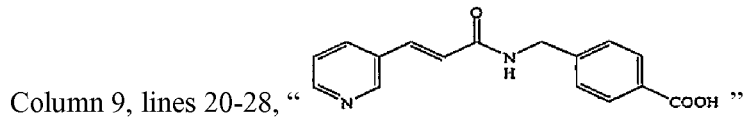 "

should read -- 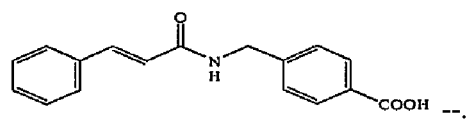 --.

Column 9, lines 51-60, " 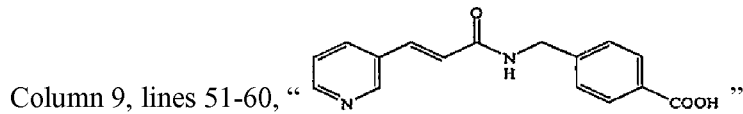 "

should read -- 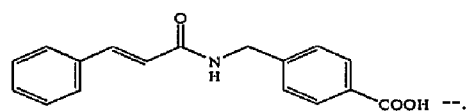 --.

IN THE CLAIMS:

Claim 1, Column 13, line 57, "perfluoralkyl" should read --perfluoroalkyl--.
Claim 9, Column 16, line 17, after "at least one" delete "a".

Signed and Sealed this

Second Day of October, 2007

JON W. DUDAS
*Director of the United States Patent and Trademark Office*

UNITED STATES PATENT AND TRADEMARK OFFICE
CERTIFICATE OF CORRECTION

PATENT NO. : 7,244,751 B2  Page 1 of 1
APPLICATION NO. : 10/770035
DATED : July 17, 2007
INVENTOR(S) : Xian-Ping Lu et al.

It is certified that error appears in the above-identified patent and that said Letters Patent is hereby corrected as shown below:

Column 9, lines 51-60,

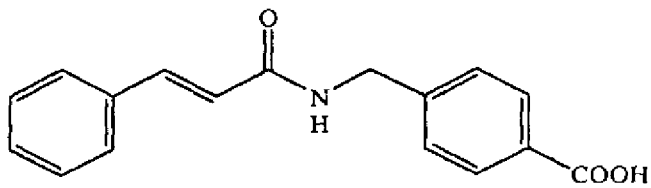

should read

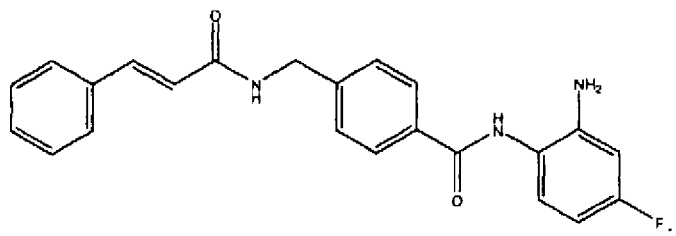

Signed and Sealed this

Thirty-first Day of March, 2009

JOHN DOLL
*Acting Director of the United States Patent and Trademark Office*